United States Patent [19]

Musick et al.

[11] Patent Number: 4,484,043

[45] Date of Patent: Nov. 20, 1984

[54] SWITCH APPARATUS RESPONSIVE TO PRESSURE OR DISTORTION

[75] Inventors: Jeff L. Musick; Robert D. Blaker; David G. Blaker, Jr., all of Tulsa, Okla.

[73] Assignee: Bed-Check Corporation, Tulsa, Okla.

[21] Appl. No.: 429,047

[22] Filed: Sep. 30, 1982

[51] Int. Cl.$^3$ .............................................. H01H 3/02
[52] U.S. Cl. ................................ 200/85 R; 200/86 R
[58] Field of Search ............... 200/85 R, 85 A, 86 R, 200/86 A

[56] References Cited

U.S. PATENT DOCUMENTS

| | | | |
|---|---|---|---|
| 3,478,311 | 11/1969 | Czingula | 200/86 R X |
| 4,020,482 | 4/1977 | Feldl | 200/85 R X |
| 4,086,458 | 4/1978 | Dickey | 200/85 R |
| 4,137,116 | 1/1979 | Miller | 200/86 R |
| 4,401,896 | 8/1983 | Fowler et al. | 200/86 R X |

Primary Examiner—J. R. Scott
Attorney, Agent, or Firm—Head, Johnson & Stevenson

[57] ABSTRACT

An apparatus for monitoring the presence of a patient in a hospital bed including an elongated, thin, generally rectangular base member of insulating flexible material, such as high-density polyethylene foam, having a generally rectangular cutout opening therein, a rectangular, thin, electrically conductive member affixed to each surface of the base, the base serving to normally maintain the conductive elements spaced apart from each other, a plastic cover cemented to the exterior surface of each of the conductive elements, the edges of the plastic cover being sealed around the full periphery of the device, a cable having two conductors, one conductor being attached to each of the conductive members, the device being generally about 4 inches wide and 34 inches long so that it may be positioned under a patient in a hospital bed, the weight of the patient serving to distort the device so that the conductive members are in contact, providing a closed signal, and the device being sufficiently rigid so that in the absence of a patient the conductive members are not in contact, thereby the absence of a patient from a hospital bed can be indicated when the device is connected to suitable circuitry.

1 Claim, 3 Drawing Figures

U.S. Patent  Nov. 20, 1984  4,484,043
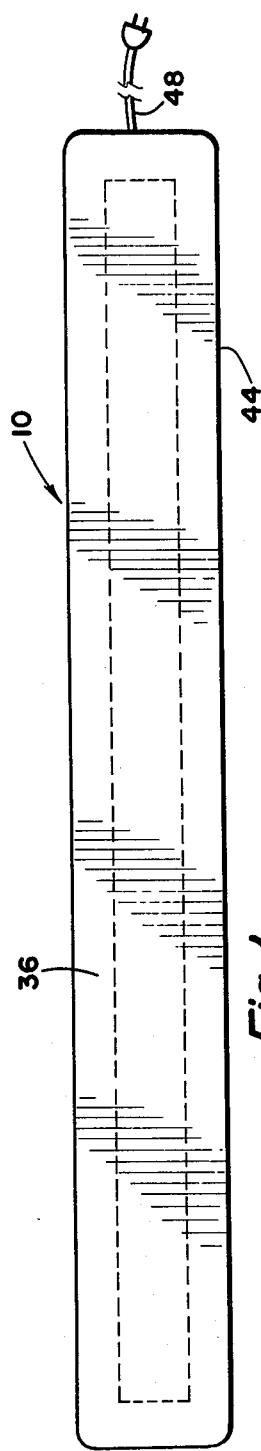
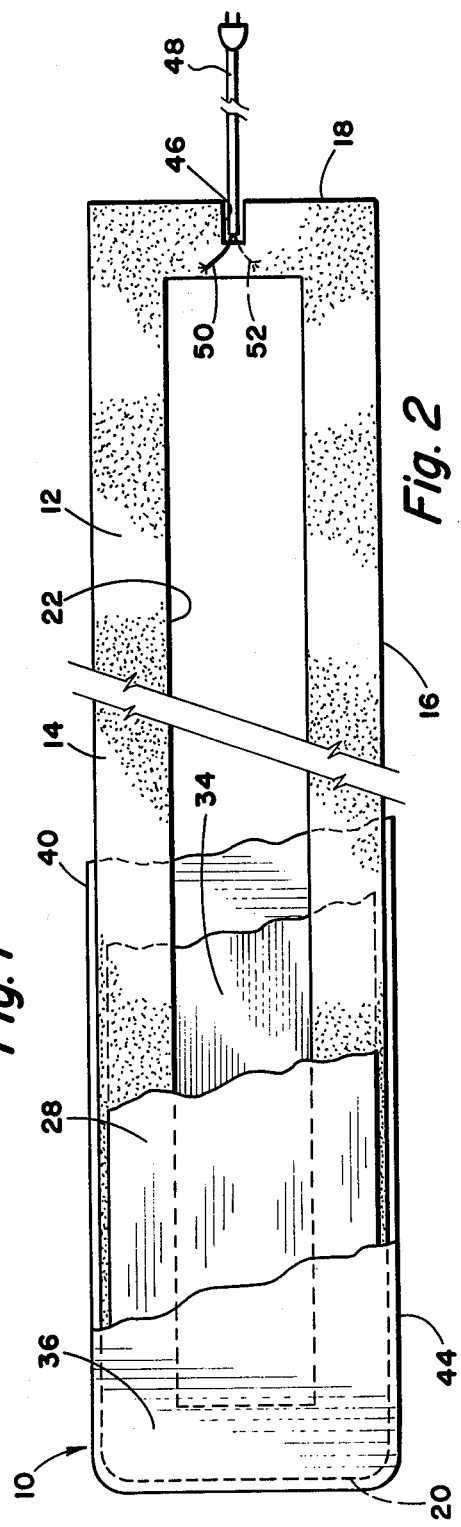
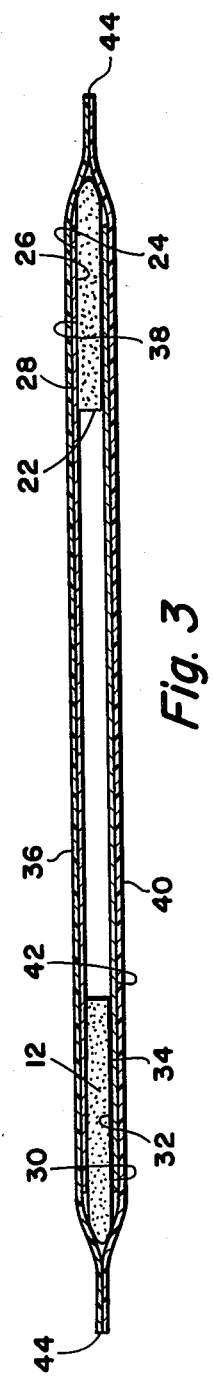

SWITCH APPARATUS RESPONSIVE TO PRESSURE OR DISTORTION

SUMMARY OF THE INVENTION

One continuous problem encountered in hospitals is that of patients evacuating a hospital bed when the patient is not of a condition so that he or she can be safely trusted out of bed. Many instances have been reported of elderly or infirmed patients evacuating hospital beds and falling, breaking bones or causing injury to themselves. Other patients are sometimes disoriented and confused because of an unfamiliar environment or the effect of drugs utilized for treatment purposes and can wander about, even sometimes leaving the hospital. For these reasons, it is important that attendants be apprised if a patient leaves a hospital bed. To provide equipment to accomplish this purpose, bed monitoring devices have been developed such as previously issued U.S. Pat. Nos. 4,179,692 and 4,295,133.

In order for electronic circuitry to function properly to indicate the evacuation of a bed by a patient, a convenient and dependable switch mechanism must be provided to open and close a circuit. The present invention provides an improved switch apparatus for this purpose and particularly one which is economical to construct, easy to use, and is more dependable than previously known types of switching devices.

The switch apparatus includes an elongated, thin, generally rectangular base member of insulating flexible material such as high-density polyethylene foam. The base portion is preferably about 1/16 inch thick and 3½ to 5 inches wide and about 25 to 40 inches long. Formed in the base member is a generally rectangular cutout opening which is preferably about 1¾ to 2¼ inches wide and of a length about 1¼ to 2 inches less than the length of the base member.

Secured on opposite faces of the base member is a first and second generally rectangular, thin, electrically conductive member. The electrically conductive members may be such as foil or foil backed with plastic, or metalized plastic material. These are secured to the base member such as by adhesive. The base member thereby supports the conductive elements normally spaced apart from each other about 1/16 of an inch. A cable having two conductors is provided, a conductor being connected to each of the conductive members. Over this assembly is positioned plastic cover members which are slightly longer and wider than the base member and the conductive elements so that the cover members may be sealed along the peripheral edges, thereby completely sealing the apparatus.

The conductive elements are bonded to the cover members and are held in spaced apart relationship at the opening formed in the base member as long as the apparatus is not subject to weight or distortion. It can be positioned under a patient and, more particularly, under sheets, bedding and the like positioned on top of a mattress. The device need not come into contact with the patient. When the device is placed on a bed which receives a patient, the weight of the patient will distort the apparatus, causing the conductive elements to contact each other. As long as the patient remains in the bed, the weight of the patient will cause a closed signal to be provided which, when connected to proper electrical circuits, provides an indication of the presence of a patient in the bed. When the patient evacuates the bed, the normal rigidity of the device is sufficient to cause the conductive elements to separate from each other, providing an open circuit which can be employed to indicate the absence of the patient from the bed.

DESCRIPTION OF THE DRAWING

FIG. 1 is a top plan view of an apparatus for monitoring patient presence in a hospital bed incorporating the principles of this invention.

FIG. 2 is a fragmentary plan view as in FIG. 1, broken away, to show the internal construction of the device.

FIG. 3 is a cross-sectional view taken along the line 3—3 of FIG. 1 showing more details of the construction of the apparatus.

DETAILED DESCRIPTION

Referring to the drawings, the apparatus for monitoring patient presence in a hospital bed is indicated generally by the numeral 10. It includes a base member 12 which is formed of non-electrically conductive, flexible, thin material. An ideal material for use in practicing the invention is high-density polyethylene foam. The base member 12 is of generally rectangular configuration having opposed sides 14 and 16 and ends 18 and 20. Formed in the base member is a cutout opening 22 which is generally rectangular and of dimensions about 1½ to 2½ inches less in width and length than the base member itself. In the typical embodiment of the invention the base member length, from end 18 to end 20, is about 25 to 40 inches long. The width from sides 14 to 16 is preferably about 3¾ to 5 inches. The thickness of the base member is preferably about 1/16 inch. The opening 22 is preferably about 1¾ to 2¼ inches wide and about 22½ to 38½ inches long, depending on the width and length of the base member.

The base member 12 can be described as generally rectangular, and the opening cutout 22 can likewise be described as generally rectangular. However, both may have curved corners if desired.

Affixed to the top surface 24 is the first surface 26 of a generally rectangular, thin, electrically conductive member 28. In like manner, the bottom surface 30 of the base member 12 receives the first surface 32 of a second conductive member 34. The conductive members 28 and 34 are preferably of thin metal, such as tin foil, aluminum foil or the like, or of metal surfaces bonded to a plastic backing core, or are of metalized plastic. The dimensions of the conductive members 28 and 34 are substantially equal to or slightly less than that of the base member 12.

As can be seen in FIG. 3, the base member opening 22 causes the conductive members 28 and 34 to be supported in spaced-apart relationship but without any physical object, other than air, separating them.

Positioned over the conductive members are plastic cover members. Specifically, a top plastic cover member 36 has one surface which engages and is bonded to the second surface 38 of the first conductive member 28. A bottom cover member 40 engages and is bonded to the second surface 42 of the second conductive member 34. The cover members 36 and 40 are slightly larger in both length and width than that of base member 12 so that they provide an overlapping peripheral edge 44 around the entire apparatus.

The end 18 of base member 12 has a notch 28 formed in it which receives the end portion of a cable 48. The notch may extend at an angle to the end 18 of the base member 50 so that the conductor emerges at or near edge 14 or 16. The cable has a first current carrying conductor 50 which is positioned to contact the first conductive member 28. A second conductor 52 contacts the second conductive element 34. This may be achieved by merely exposing the conductive portions 50 and 52 of the cable 48 to contact the surfaces of the conductive members as the conductive members are secured to the base member.

The apparatus is constructed in this manner. First, the base member 12 is provided with the dimensions as previously set out and with the notch 46 formed in it. An adhesive is applied to the top and bottom surfaces of the base member. Next, the cable 48 is positioned with the end in notch 46 and with conductors 50 and 52 exposed on opposed surfaces of the base member. The conductive members 28 and 34 are then positioned on the base member. The conductive members 28 and 34 thereby engage the conductors 50 and 52 respectively. Next, the cover members 36 and 40 are positioned over the conductive members with adhesive therebetween. The assembly is then pressed securely together by means of a press or rollers to bond the portions to each other. The edge 44 is sealed around the complete assembly. The switch is then completed. It can be seen that all of the elements used to construct the switch are inexpensive and the switch can be expeditiously assembled. This is important in that the device can be considered a throw-away item, that is, it will be limited in usage to one patient. Others may elect to sanitize the device for reuse, which can be easily accomplished since it is hermetically sealed and only the exterior surfaces of the cover are exposed.

The construction of the device means that when no pressure or distortion takes place it is self-rigid so that no contact is provided between the conductive members 28 and 34. However, with the weight of a patient on the device, distortion is sufficient to cause the conductive members 28 and 34 to contact at one place or another, or at a plurality of places along the length of the device, providing a closed circuit.

While the invention has been described as it particularly pertains to use in a hospital bed as an example of application of the device, it can be seen that the invention can be applied to use in the beds of nursing homes, in the home of individual users, or for any other switching purpose where pressure or distortion is to be detected. The device can be used under a carpet or a mat, or incorporated in a mat, such as for use in a burglar alarm system.

While the invention has been described with a certain degree of particularity, it is manifest that many changes may be made in the details of construction and the arrangement of components without departing from the spirit and scope of this disclosure. It is understood that the invention is not limited to the exemplified embodiments set forth herein but is to be limited only by the scope of the attached claim or claims, including the full range of equivalency to which each element thereof is entitled.

What is claimed is:

1. Switch apparatus positionable on a mattress and responsive to distortion by the weight of a patient, comprising:

an elongated, thin, generally rectangular base member of insulating flexible material, the base member being about 3¼ to 5 inches wide and about 25 to 40 inches long, and about 1/16 inch thick, the base member providing a top and bottom surface and having an elongated generally rectangular opening cut out therein, the cut out being about 1¾ to 2¼ inches wide and 23½ to 38½ inches long;

a first generally rectangular, thin, electrically conductive member having a first and second surface, the first surface being supported on said top surface of said base member;

a second generally rectangular, thin, electrically conductive member having a first and second surface, the first surface being supported on said bottom surface of said base member, said conductive members being thereby spaced parallel to each other, and of width and length not substantially greater than the width and length of said base member;

a first non-conductive, thin, generally rectangular plastic cover member affixed to said second surface of said first conductive member;

a second non-conductive, thin, generally rectangular plastic cover member affixed to said second surface of said second conductive member; and a cable having a first and second conductor, the first conductor having engagement with said first conductive member and the second conductor having engagement with said second conductive member, said first and second cover members being of length and width greater than said base member and said cover members providing overlapping edges, the end portion of said cable having said conductor portions engaging said conductive elements being positioned between said cover members, the peripheries of said cover members being sealed, the conductive members being normally supported by said base member in spaced-apart relationship by the memory of said base and said plastic cover members but which members contact each other when the apparatus is subject to bending or twisting distortion.

* * * * *